United States Patent
Zeller et al.

(10) Patent No.: US 9,492,129 B2
(45) Date of Patent: Nov. 15, 2016

(54) TRIGGERING OF INTRAORAL X-RAY SENSOR USING PIXEL ARRAY SUB-SAMPLING

(75) Inventors: Uwe Zeller, Biberach (DE); Doug Golay, Coon Rapids, IA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 370 days.

(21) Appl. No.: 12/796,235

(22) Filed: Jun. 8, 2010

(65) Prior Publication Data

US 2011/0013746 A1 Jan. 20, 2011

Related U.S. Application Data

(60) Provisional application No. 61/226,533, filed on Jul. 17, 2009.

(51) Int. Cl.
*A61B 6/14* (2006.01)
*A61B 6/00* (2006.01)
(Continued)

(52) U.S. Cl.
CPC ............. *A61B 6/145* (2013.01); *A61B 6/4233* (2013.01); *A61B 6/5205* (2013.01); *A61B 6/545* (2013.01); *A61B 2562/02* (2013.01); *A61B 2562/0233* (2013.01); *A61B 2562/046* (2013.01); *H04N 5/32* (2013.01); *H04N 5/361* (2013.01)

(58) Field of Classification Search
CPC .... A61B 6/145; A61B 6/4233; A61B 6/545; G01T 1/247
USPC ......................................................... 378/98.8
See application file for complete search history.

(56) References Cited

U.S. PATENT DOCUMENTS 3,023,267 A   2/1962   Eager et al.
3,843,831 A   10/1974  Hutchinson et al.
(Continued)

FOREIGN PATENT DOCUMENTS

CN   1156376    8/1997
DE   19815637   10/1998
(Continued)

OTHER PUBLICATIONS

Translation for JP 2000-175906 published on Jun. 27, 2000.*
(Continued)

*Primary Examiner* — Glen Kao
*Assistant Examiner* — Chih-Cheng Kao
(74) *Attorney, Agent, or Firm* — Michael Best & Friedrich LLP (57) ABSTRACT

Automatic triggering of an intraoral x-ray sensor used in a dental x-ray imaging system. The intraoral sensor has an array of pixels. The array of pixels has a plurality of lines of pixels, and each of the pixels generates an electrical signal correlated to x-ray radiation that impinges that pixel. An electronic control unit is connected to the intraoral sensor to receive electric signals from the array of pixels. The electronic control unit destructively reads pixel clusters in one or more of the plurality of lines of pixels. The electronic control unit is configured to generate a dose-correlated signal based on the signals from each of the pixel clusters in each of the one or more lines of pixels and initiate capture of an image generated with information from each of the pixels in the array of pixels, when the combined signal exceeds a predetermined threshold.

5 Claims, 7 Drawing Sheets

(51) Int. Cl.
H04N 5/32          (2006.01)
H04N 5/361         (2011.01)

(56) References Cited

U.S. PATENT DOCUMENTS

| | | |
|---|---|---|
| 4,057,732 A | 11/1977 | Klauser |
| 4,259,583 A | 3/1981 | Albert |
| 4,593,400 A | 6/1986 | Mouyen |
| 4,866,750 A | 9/1989 | Chavarria et al. |
| 5,053,873 A * | 10/1991 | Taniji .................... 348/243 |
| 5,220,130 A | 6/1993 | Walters |
| 5,331,166 A | 7/1994 | Yamamoto et al. |
| 5,434,418 A | 7/1995 | Schick |
| 5,436,476 A * | 7/1995 | Hynecek ................. 257/223 |
| 5,471,515 A | 11/1995 | Fossum et al. |
| 5,510,623 A | 4/1996 | Sayag et al. |
| 5,513,252 A | 4/1996 | Blaschka et al. |
| 5,514,873 A | 5/1996 | Schulze-Ganzlin et al. |
| 5,519,751 A | 5/1996 | Yamamoto et al. |
| 5,572,566 A | 11/1996 | Walters |
| 5,574,250 A | 11/1996 | Hardie et al. |
| 5,677,537 A | 10/1997 | Pfeiffer |
| 5,691,539 A | 11/1997 | Pfeiffer |
| 5,694,448 A | 12/1997 | Morcom |
| 5,757,011 A | 5/1998 | Whitebook et al. |
| 5,784,429 A | 7/1998 | Arai |
| 5,789,711 A | 8/1998 | Gaeris et al. |
| 5,887,049 A | 3/1999 | Fossum |
| 5,894,129 A * | 4/1999 | Pool .................... 250/370.09 |
| 5,912,942 A | 6/1999 | Schick et al. |
| 6,002,742 A | 12/1999 | Nelvig |
| 6,011,251 A | 1/2000 | Dierickx et al. |
| 6,030,119 A | 2/2000 | Tachibana et al. |
| 6,033,111 A | 3/2000 | Winters et al. |
| 6,042,267 A | 3/2000 | Muraki et al. |
| 6,069,935 A | 5/2000 | Schick et al. |
| 6,074,503 A | 6/2000 | Clark et al. |
| 6,101,076 A | 8/2000 | Tsai et al. |
| 6,127,684 A | 10/2000 | Kaifu |
| 6,134,298 A | 10/2000 | Schick et al. |
| 6,169,781 B1 | 1/2001 | Doebert et al. |
| 6,203,195 B1 | 3/2001 | Willis |
| 6,244,866 B1 | 6/2001 | Campbell |
| 6,271,880 B1 | 8/2001 | Kameshima et al. |
| 6,307,915 B1 | 10/2001 | Frojdh |
| 6,320,934 B1 | 11/2001 | Carroll et al. |
| 6,343,875 B1 | 2/2002 | Eppinger et al. |
| 6,404,854 B1 * | 6/2002 | Carroll et al. ............ 378/98.8 |
| 6,462,268 B1 | 10/2002 | Hazy et al. |
| 6,527,442 B2 | 3/2003 | Carroll |
| 6,652,141 B1 | 11/2003 | Cianciosi |
| 6,744,068 B2 | 6/2004 | Fossum et al. |
| 6,797,960 B1 | 9/2004 | Spartiotis et al. |
| 6,801,592 B1 | 10/2004 | Christensen |
| 6,811,312 B2 | 11/2004 | Bratslavsky et al. |
| 6,833,548 B2 | 12/2004 | Homme et al. |
| 6,898,268 B2 | 5/2005 | Makila et al. |
| 6,919,569 B2 | 7/2005 | Homme et al. |
| 6,924,486 B2 | 8/2005 | Schick et al. |
| 6,932,505 B2 | 8/2005 | Yao et al. |
| 6,972,411 B2 | 12/2005 | Schick et al. |
| 6,974,253 B2 | 12/2005 | Ihalainen |
| 6,984,788 B2 | 1/2006 | Grögl et al. |
| 7,006,600 B1 | 2/2006 | Krema et al. |
| 7,016,466 B2 | 3/2006 | Rinaldi et al. |
| 7,033,075 B2 | 4/2006 | Landis et al. |
| 7,036,985 B2 | 5/2006 | Puente et al. |
| 7,072,443 B2 | 7/2006 | Schick et al. |
| 7,081,607 B1 * | 7/2006 | Koizumi .................... 250/208.1 |
| 7,090,395 B2 | 8/2006 | Glazer |
| 7,091,465 B2 | 8/2006 | Miyaguchi |
| 7,172,339 B2 | 2/2007 | Diederich |
| 7,193,219 B2 | 3/2007 | Schick et al. |
| 7,195,395 B2 | 3/2007 | Quarry et al. |
| 7,210,847 B2 | 5/2007 | Hack |
| 7,281,847 B2 | 10/2007 | Kokkaliaris et al. |
| 7,360,948 B2 | 4/2008 | Razzano et al. |
| 7,425,095 B2 | 9/2008 | Schmulenson et al. |
| 7,462,807 B2 | 12/2008 | Caupain et al. |
| 7,506,082 B2 | 3/2009 | Kim |
| 7,563,026 B2 | 7/2009 | Mandelkern et al. |
| 7,608,834 B2 | 10/2009 | Boucly et al. |
| 7,659,516 B2 | 2/2010 | Korthout et al. |
| 7,711,173 B2 | 5/2010 | Inglese |
| 7,915,589 B2 | 3/2011 | Takenaka et al. |
| 8,119,990 B2 | 2/2012 | Zeller |
| 8,324,587 B2 | 12/2012 | Zeller |
| 8,366,318 B2 | 2/2013 | Zeller et al. |
| 9,259,197 B2 | 2/2016 | Zeller et al. |
| 2003/0121694 A1 | 7/2003 | Grogl et al. |
| 2004/0065836 A1 | 4/2004 | Schick et al. |
| 2004/0188625 A1 | 9/2004 | Schulze-Ganzlin |
| 2005/0040395 A1 * | 2/2005 | Hong ....................... 257/40 |
| 2006/0093869 A1 | 5/2006 | Meguro et al. |
| 2006/0256920 A1 * | 11/2006 | Tsujii ................... A61B 6/02 |
| | | 378/114 |
| 2006/0257816 A1 | 11/2006 | Klemola et al. |
| 2006/0262461 A1 | 11/2006 | Wood |
| 2007/0147675 A1 | 6/2007 | Ulrici et al. |
| 2007/0176109 A1 * | 8/2007 | Bell ...................... 250/370.09 |
| 2007/0286335 A1 | 12/2007 | De Godzinsky |
| 2008/0001094 A1 | 1/2008 | Korthout et al. |
| 2008/0095321 A1 | 4/2008 | Calderwood et al. |
| 2008/0118028 A1 | 5/2008 | Stantchev |
| 2010/0258333 A1 | 10/2010 | Horan et al. |
| 2013/0000944 A1 | 1/2013 | Zeller et al. |
| 2013/0092844 A1 | 4/2013 | Zeller |

FOREIGN PATENT DOCUMENTS

| | | |
|---|---|---|
| EP | 0415075 | 3/1991 |
| EP | 0756416 | 1/1997 |
| EP | 1230896 | 8/2002 |
| EP | 1252762 | 10/2002 |
| EP | 1255401 | 11/2002 |
| EP | 1378201 | 1/2004 |
| EP | 1623673 | 2/2006 |
| EP | 1746442 | 1/2007 |
| EP | 1803400 | 7/2007 |
| GB | 1514851 | 6/1978 |
| JP | 08-000603 | 1/1996 |
| JP | H09-107503 | 4/1997 |
| JP | 2000175906 | 6/2000 |
| JP | 2003126072 | 5/2003 |
| JP | 2005087281 | 4/2005 |
| JP | 2006-263483 | 10/2006 |
| JP | 2008132216 | 6/2008 |
| JP | 2011223508 | 11/2011 |
| WO | 92/22188 | 12/1992 |
| WO | 96/32064 | 10/1996 |
| WO | 01/58148 | 8/2001 |
| WO | 02/063338 | 8/2002 |
| WO | 03/032839 | 4/2003 |
| WO | 2006/004528 | 1/2006 |
| WO | 2006/008339 | 1/2006 |
| WO | 2006/034978 | 4/2006 |
| WO | 2006/089003 | 8/2006 |
| WO | 2006/093869 | 9/2006 |
| WO | 2006/103126 | 10/2006 |
| WO | 2007/003495 | 1/2007 |
| WO | 2007/022246 | 2/2007 |
| WO | 2007/030381 | 3/2007 |
| WO | 2007/044412 | 4/2007 |
| WO | 2007/142925 | 12/2007 |
| WO | 2008/058865 | 5/2008 |
| WO | 2008/103460 | 8/2008 |
| WO | 2009/055136 | 4/2009 |
| WO | 2009/058467 | 5/2009 |
| WO | 2009/058468 | 5/2009 |
| WO | 2011008421 | 1/2011 |
| WO | WO 2011/008421 | 1/2011 |
| WO | WO 2011/008422 | 1/2011 |

(56) References Cited

FOREIGN PATENT DOCUMENTS

OTHER PUBLICATIONS

Nixon, R.H., et al., "128X128 CMOS Photodiode-Type Active Pixel Sensor with On-Chip Timing, Control and Signal Chain Electronics", SPIE, vol. 2415, pp. 117-123, 1995.
Mendis, S.K., et al., "A 128X128 CMOS Active Pixel Image Sensor for Highly Integrated Imaging Systems", IEEE IEDM Technical Digest, pp. 583-586, 1993.
Andoh, F., et al., "A 250,000-Pixel Image Sensor with FET Amplification at Each Pixel for High-Speed Television Cameras", IEEE ISSCC Digest of Technical Papers, pp. 212-213, Feb. 1990.
Fossum, Eric, R., "CMOS Image Sensors: Electronic Camera-On-A-Chip", IEEE Transactions on Electron Devices, vol. 44, No. 10, pp. 1689-1698, Oct. 1997.
Universal Serial Bus Specification, Chapter 6—Mechanical, Revision 2.0, Apr. 27, 2000.
Spartiotis, Konstantinos, et al., "A Directly Converting High-Resolution Intra-Oral X-Ray Imaging Sensor", Nuclear Instruments and Methods in Physics Research, Section A, 501, pp. 594-601, Elsevier Science B.V., 2003.
Hong, Soonil, et al, "Development and Evaluation of a CMOS Sensor-Based Digital Intra-Oral Radiographic System", IEEE Transactions on Nuclear Science, vol. 52, No. 1, Feb. 2005.
International Search Report and Written Opinion, International Application No. PCT/US2010/039322, mailed Aug. 17, 2010.
International Search Report and Written Opinion, International Application No. PCT/US2010/039324, mailed Oct. 8, 2010.
EP10800232.0 Extended European Search Report dated Dec. 21, 2012 (3 pages).
Office Action from the Japanese Patent Office for Application No. 2012520649 dated Jul. 23, 2013 (5 pages).
United States Patent Office Action for U.S. Appl. No. 12/605,624 dated Jun. 23, 2011 (9 pages).
United States Patent Office Examiner Interview Summary for U.S. Appl. No. 12/605,624 dated Aug. 4, 2011 (3 pages).
United States Patent Office Notice of Allowance for U.S. Appl. No. 12/605,624 dated Oct. 5, 2011 (7 pages).
United States Patent Office Action for U.S. Appl. No. 13/358,125 dated Mar. 22, 2012 (6 pages).
United States Patent Office Notice of Allowance for U.S. Appl. No. 13/358,125 dated Sep. 5, 2012 (6 pages).
United States Patent Office Action for U.S. Appl. No. 13/692,323 dated Feb. 15, 2013 (9 pages).
United States Patent Office Action for U.S. Appl. No. 13/692,323 dated May 29, 2014 (12 pages).
United States Patent Office Action for U.S. Appl. No. 13/692,323 dated Oct. 18, 2013 (8 pages).
Chinese Patent Office Action for Application No. 201080032476.3 dated Sep. 2, 2013 (12 pages, English translation included).
Office Action from the United States Patent and Trademark Office for U.S. Appl. No. 12/796,251 dated Jun. 21, 2012 (10 pages).
Office Action from the Japanese Patent Office for Application No. 2012520649 dated Mar. 25, 2014 (4 pages).
EP09174091.0 Search Report dated Apr. 18, 2013 (5 pages).
Japanese Patent Office Action for Application 2009-246319 dated Mar. 5, 2014 (3 pages English Translation only).
Japanese Patent Office Action for Application 2009-246319 dated May 27, 2013 (3 pages English Translation only).
Second Office Action from the State Intellectual Property Office of the People's Republic of China for Application No. 2010800324763 dated May 12, 2014 (28 pages).
Third Office Action with English translation from the State International Property Office of the People's Republic of China for Application No. 201080032476.3 dated Nov. 5, 2014 (24 pages).
4th Office Action from the State Intellectual Property Office of the People's Republic of China for Application No. 201080032476.3 dated May 14, 2015 (6 pages).
Japanese Patent Office Action for Application No. 2012-520649 dated Feb. 27, 2015 (7 pages including English Translation).
Office Action from the United States Patent and Trademark Office for U.S. Appl. No. 13/692,323 dated May 29, 2014 (16 pages).
Final Office Action from the United States Patent and Trademark Office for U.S. Appl. No. 13/692,323 dated Feb. 10, 2015 (24 pages).
Office Action from the United States Patent and Trademark Office for U.S. Appl. No. 13/611,572 dated Apr. 9, 2015 (15 pages).
Final Office Action from the United States Patent and Trademark Office for U.S. Appl. No. 13/611,572 dated Nov. 28, 2014 (15 pages).
Notice of Allowance from the United States Patent and Trademark Office for U.S. Appl. No. 13/611,572 dated Oct. 6, 2015 (10 pages).
Office Action from the United States Patent and Trademark Office for U.S. Appl. No. 13/692,323 dated Jun. 17, 2015 (9 pages).
Office Action from the United States Patent and Trademark Office for U.S. Appl. No. 13/611,572 dated Jul. 8, 2015 (10 pages).
Office Action from the European Patent Office for Application No. 09174091.0 dated Nov. 6, 2015 (7 pages).
Notice of Preliminary Rejection from the Korean International Patent Office for Application No. 10-2009-0102361 dated Nov. 10, 2015 (7 pages).
Final Office Action with English translation from the Japanese Patent Office for Application No. 2012-520649 dated Oct. 2, 2015 (6 pages).
Notice of Preliminary Rejection from The Korean International Patent Office for Application No. 10-2012-7004070 dated Jun. 1, 2016 (7 pages).
Office Action from the United States Patent and Trademark Office for U.S. Appl. No. 15/006,893 dated May 16, 2016 (8 pages).
Office Action from the United States Patent and Trademark Office for U.S. Appl. No. 13/692,323 dated Jul. 28, 2016 (13 pages).
Notice of Allowance from the United States Patent and Trademark Office for U.S. Appl. No. 15/006,893 dated Aug. 8, 2016 (10 pages).

* cited by examiner

TRIGGERING OF INTRAORAL X-RAY SENSOR USING PIXEL ARRAY SUB-SAMPLING

CROSS-REFERENCE TO RELATED APPLICATIONS

The present application claims priority to U.S. Provisional Patent Application Ser. No. 61/226,533, filed Jul. 17, 2009, the entire contents of which is hereby incorporated by reference. The subject matter of this application is also related to U.S. patent application Ser. No. 12/605,624, filed Oct. 26, 2009, U.S. Provisional Patent Application Ser. No. 61/108,552, filed Oct. 27, 2008, and U.S. Provisional Patent Application Ser. No. 61/226,556, filed Jul. 17, 2009, the entire contents of which are hereby incorporated by reference.

BACKGROUND

The present invention relates to x-ray imaging, including dental x-ray imaging. More particularly, embodiments of the invention relate to automatic triggering of an x-ray sensor used in dentistry.

X-rays have been used in dentistry to image teeth and parts of the mouth for many years. In general, the process involves generating x-rays and directing the x-rays at the patient's mouth. The x-rays are attenuated differently by different parts of the mouth (e.g., bone versus tissue) and this difference in attenuation is used to create an image, such as on film or by using electronic image sensor. In most cases, the x-ray source is triggered manually. That is, the capturing of an image is initiated by a technician or other person by, for example, activating a switch. In the case of film-based systems, the image is captured as soon as the film is exposed to x-ray radiation. So, there is no need to "activate" the film. Once the x-ray source is activated and the x-rays reach the film, an image is captured.

In electronic systems, the particular image captured depends on at least two factors: activation of the x-ray source and "activation" of the sensor. What constitutes "activation" of the sensor can vary based upon the type of sensor used, but in most cases "activation" occurs when a command is provided to the sensor to either store or output its current image data (referred to herein as "image capture"). So, in some systems, there is an electrical link between the x-ray source and the sensor such that when the x-ray source is activated a command is sent (simultaneously or nearly simultaneously) to the sensor to perform an image capture. Thus, it is possible to generate a burst of x-ray radiation and be assured that an image will be captured by the sensor during the relatively short period of x-ray exposure.

SUMMARY

A number of technologies have been developed to provide automatic activation or triggering of x-ray sensors without needing an electrical or similar link between the trigger of the x-ray source and the sensor. For example, U.S. Pat. No. 5,694,448 discloses a solid-state imaging device that is "clocked out" during a wait period prior to irradiation from an x-ray source. A signal derived from a charge-coupled device is compared to a threshold to determine the onset of irradiation. If the threshold is met or exceeded, image capture or acquisition occurs. While the sensor disclosed in the '448 patent eliminates the need for an electrical link between the x-ray source and the sensor, it is not fully satisfactory.

One challenge associated with automatic triggering systems relates to the alignment between the x-ray source and the sensor. In many instances, even with the use of a positioning system or mechanism, x-ray sensors (particularly those placed in the mouth (i.e., an intra-oral sensor)) are often misaligned. Thus, only a portion of the x-ray sensor is exposed to radiation. In many instances, this partial exposure is not sufficient to cause a simple threshold-based trigger to initiate image capture. Thus, a misalignment may not be recognized until the x-ray technician attempts to review images that he or she believes to have been created only to discover that no such images have been created. The technician may then try to realign the x-ray source and sensor and reinitiate the imaging process. However, it may take several attempts to capture a usable image and each attempt exposes the patient to additional doses of x-ray radiation. As is well-known, x-ray radiation can have adverse effects on an individual's health. So, unnecessary exposure to x-rays should be avoided.

Another challenge associated with automatic triggering systems is the relatively large variation in x-ray doses that are provided to patients. The received dose is a function of the x-ray dose rate, the x-ray exposure time, the x-ray exposure projection, and the x-ray attenuation of the object. The received dose at the sensor is the integral of the time-depending dose rate over time. The variation in dosage is caused by a number of factors including differences in x-ray sources. X-ray sources are manufactured by a number of different manufacturers and their designs and specifications have changed over time. Thus, the intensity of their outputs varies. For example, older x-ray machines usually generate relatively high x-ray doses while newer machines generate lower doses. Also, some older x-ray machines use pulsed exposure schemes while newer machines may deliver a steady time constant dose and dose rate. The variation in dosage is also a consequence of variation in anatomy (from patient to patient) and the distance of the source to the patient. As is known, the x-ray dose and dose rate are dependent on the distance (d) between the source and the patient by a factor of $d^2$.

Embodiments of the invention provide, among other things, a method of automatically triggering an intraoral x-ray sensor using pixel array sub-sampling. The method includes directing x-ray radiation toward the intraoral sensor. When x-ray radiation impinges a pixel in the array of pixels, an electrical signal correlated to the x-ray radiation that impinges the pixel is generated. The method also includes processing electrical signals generated by one or more pixels in the array of pixels in a processor or similar electronic device by destructively reading first and second pixel clusters located at a perimeter of the array of pixels in one or more of the plurality of lines of pixels. Then, a combined signal based on the signals from each of the first and second pixel clusters in each of the one or more lines of pixels is generated. When the combined signal exceeds a predetermined threshold, capture of an image generated with information from all of the pixels in the array of pixels is initiated.

In another embodiment, the invention provides an intraoral x-ray system. The system includes an intraoral sensor having an array of pixels. The array of pixels has a plurality of lines of pixels. Each of the pixels generates an electrical signal correlated to x-ray radiation that impinges that pixel. A processor or similar electronic device receives electric signals from the array of pixels. The processor destructively reads first and second pixel clusters in one or more of the plurality of lines of pixels. Each of the first and second pixel clusters is located at a perimeter of the array of pixels. In one embodiment, the processor generates a combined signal based on the signals from each of the first and second pixel clusters in each of the one or more lines of pixels and initiates capture of an image (which is generated with information from all of the pixels in the array of pixels) when the combined signal exceeds a predetermined threshold. In another embodiment, the processor generates a combined signal based on the first and second pixel clusters and initiates image capture when the combined signal exceeds a threshold.

In another embodiment, the invention provides an intraoral x-ray system. The intraoral x-ray system includes an array of pixels including a perimeter, a processor coupled to the array of pixels, and cluster select lines. Each pixel of the array of pixels generates an electrical signal correlated to x-ray radiation that impinges that pixel. The array of pixels includes at least a first portion of pixels arranged in a first cluster at a first side of the perimeter and a second portion of pixels arranged in a second cluster at a second side of the perimeter. The second side of the perimeter is opposite of the first side of the perimeter. The cluster select lines, when enabled, couple the processor to at least one of the first cluster and the second cluster to enable the processor to determine an amount of electrical signal generated at the at least one of the first cluster and second cluster. The processor reads the array of pixels if the processor determines that the amount of electrical signal generated crosses a threshold.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
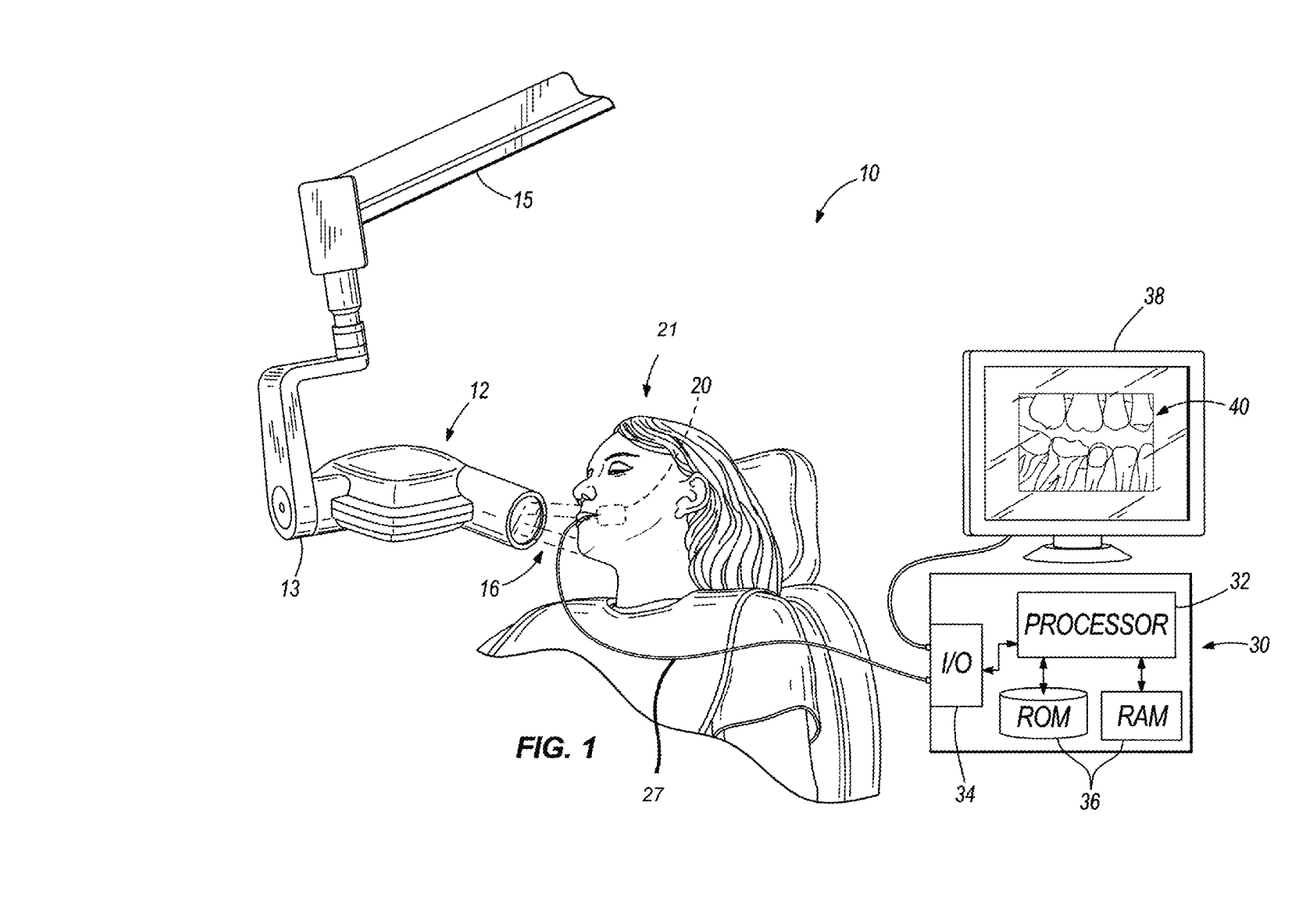
FIG. 1 is a schematic illustration of a dental x-ray system including an x-ray source, an intraoral sensor located in a patient's mouth, and a computer connected to the intraoral sensor.
Figure 1A:
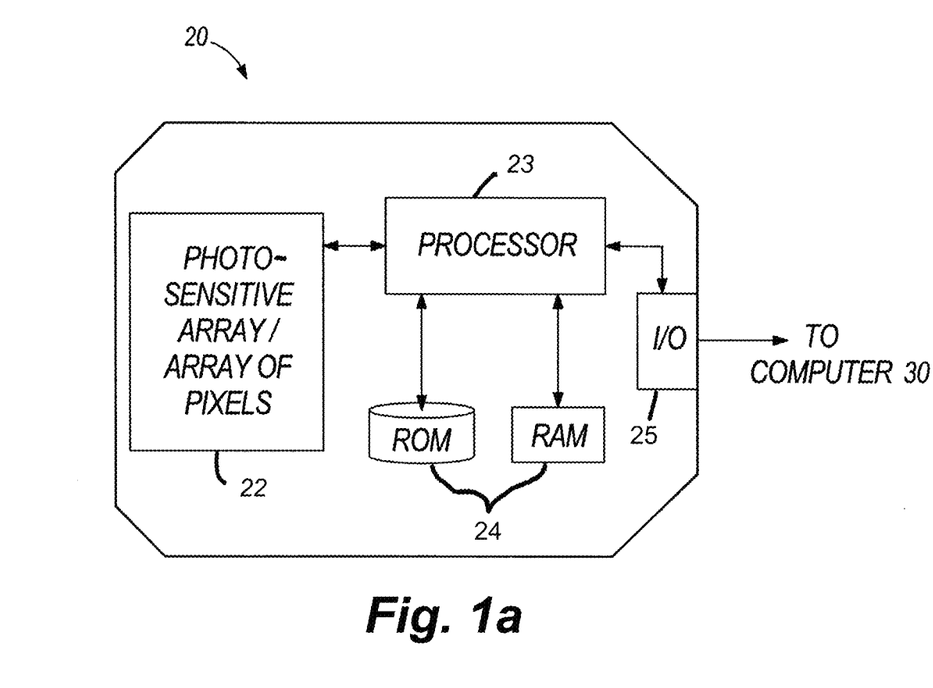
FIG. 1a is a schematic illustration of the intraoral sensor shown in FIG. 1 showing internal components of the sensor, including an array of pixels and a processor.

FIG. 1 illustrates a dental x-ray system 10. The system includes an x-ray source 12. In the embodiment shown, the source is located on an end 13 of a mechanical arm 15. When activated, the x-ray source 12 generates an x-ray stream 16 that has a generally circular cross-section. (Of course, x-rays are generally invisible, but a representation of a stream is illustrated to facilitate understanding of the invention.) In many applications, a collimator is used to reduce the size of the stream and generate a smaller x-ray stream having a rectangular cross-section. A collimator may be used with a mechanical positioning device to help align the x-ray stream with an x-ray sensor. As shown in FIG. 1, the arm 15 is positioned (e.g., by an operator) so that the x-ray stream is directed to an intraoral sensor 20. The intraoral sensor 20 is shown located in the mouth of a patient 21. In some embodiments, the intraoral sensor 20 includes a scintillator that coverts x-ray radiation to visible light. In other embodiments, the sensor 20 is configured to convert x-rays to electrons without a scintillator. As best seen by reference to FIG. 1A, the sensor 20 also includes an array of pixels 22. Each pixel produces an electric signal in response to light (from the scintillator) or x-ray radiation impinged upon it. In one embodiment, the sensor 20 includes one or more "onboard" analog-to-digital converters to covert analog signals generated by the pixels to digital signals. These signals are provided to a processor 23 (such as a programmable, electronic microprocessor or similar device). In the embodiment shown, the processor 23 is connected to memory 24 (ROM and RAM) and an input-output interface 25. The sensor also includes one or more electronic circuits for power supply, driving the array of pixels, and driving the output (e.g., circuits located in the I/O interface 25). As discussed in greater detail below, in the embodiment illustrated, the processor 23 controls image capture or triggering of the sensor 20.

Referring back to FIG. 1, a wire, cable, or similar connector 27 of the sensor 20 connects the sensor 20 to a computer 30. The computer 30 includes various components, including a processor or similar electronic device 32, an input/output interface 34, and memory 36 (e.g., RAM and ROM). In one particular embodiment, the input/output interface 34 is a USB connection and the connector 27 is a USB cable. FIG. 1 illustrates that image data captured by the sensor 20 and processed by the computer 30 is sent to a display 38 and viewed as image 40. (Image 40 is drawn more distinctly than an x-ray image would typically appear.)

The location of the intraoral sensor 20 in the patient's mouth determines what part of the patient's anatomy can be imaged (e.g., the upper jaw versus the lower jaw or the incisors versus the molars.) An x-ray operator places (or assists the patient in placing) the intraoral sensor at a desired location with the patient's mouth. Various sensor holders (including those that are used with or that include a collimator) may be used to keep the sensor 20 in the desired location until an image is created or captured. For example, some holders are designed so that the patient bites the holder with his or her teeth and maintain the position of the sensor by maintaining a bite on the holder. After the sensor is positioned behind the desired anatomical structure, and the x-ray field to be generated by the x-ray source 12 is aligned with the sensor, it is possible that the source and sensor will, nevertheless, become misaligned. Misalignment can be caused by the patient moving his or her head, moving the intraoral sensor (by re-biting the holder, moving his or her tongue, etc.), and other causes.

Figure 2A:
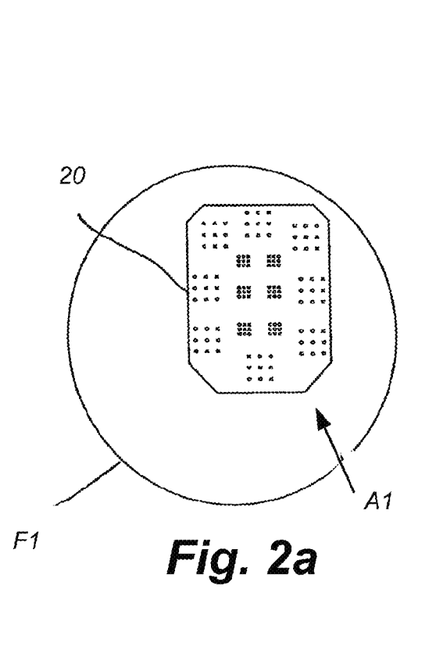
FIGS. 2a through 2c illustrate variations in alignment between the field of x-ray radiation generated by the x-ray source and the intraoral sensor.
Figures 2B, 2C:
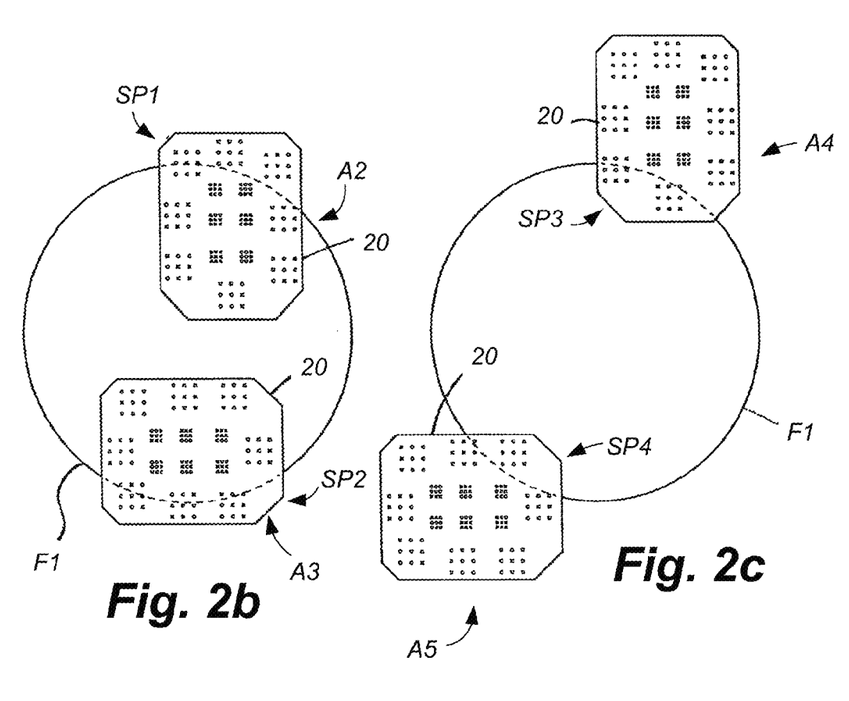

FIG. 2a illustrates an alignment A1 in which the sensor 20 is located entirely within an x-ray field F1 produced by the x-ray source 12. FIG. 2b illustrates two alignments A2 and A3, where the sensor 20 is located mostly within the x-ray field F1, but a portions of the sensor (either SP1 or SP2) are located outside of the field F1. FIG. 2c illustrates two alignments A4 and A5, where the sensor 20 is located mostly outside the x-ray field F1, but portions (either SP3 or SP4) are located inside of the field F1.

As noted above, in many known systems image capture is triggered based on manual activation of a switch or upon the output of an image sensor (i.e., the output from all the pixels) exceeding a predetermined threshold. In embodiments of the invention, triggering of image capture or acquisition is based on sub-sampling particular pixel clusters located within an image sensor.

Figure 3A:
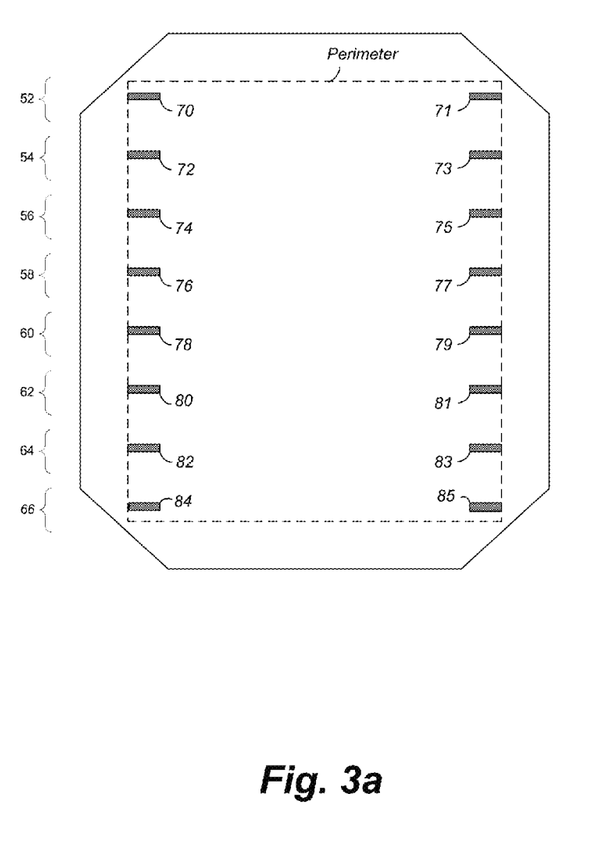
FIG. 3a is a schematic illustration of the array of pixel elements in the intraoral x-ray sensor shown in FIG. 1

FIG. 3a illustrates the alignment of pixels in the sensor 20. As noted, the sensor 20 includes a plurality of pixels and the processor 23 receives information from the pixels. The processor reads out data from the pixels in the array of pixels of the sensor. FIG. 3a illustrates eight lines of pixels of the sensor (lines 52, 54, 56, 58, 60, 62, 64, and 66.) Each line includes a first cluster of pixels and a second cluster of pixels. For example, line 52 includes clusters 70 and 71. Line 54 includes clusters 72 and 73. Lines 56, 58, 60, 62, 64, and 66 include clusters 74 and 75, 76 and 77, 78 and 79, 80 and 81, 82 and 83, and 84 and 85, respectively. In the embodiment shown, each pixel cluster 70-85 includes 32 pixels.

Each of the pixel clusters in each line of the array of pixels is located at the edge or perimeter P or the sensor. For example, in the embodiment shown in FIG. 3a, each of the pixel clusters on the left-hand side ("LHS") of the sensor 20 (i.e., clusters 72, 74, 76, 78, 80, 82, and 84) includes the first 32, left-most pixels on the line and each of the clusters on the right-hand side ("RHS") of the sensor 20 (i.e., clusters 71, 73, 75, 77, 79, 81, 83, and 85) includes the last 32, right-most pixels on the line. The pixel clusters in each of the lines of pixels and in the general configuration shown in FIG. 3a are referred to as the "perimeter pixels."

In one embodiment of the invention, the processor 23 carries out a rolling-shutter mode scanning of the perimeter pixels. In such an embodiment, the pixel integration time is set at a predetermined amount and one cluster is sampled at some fraction of this time. For example, the integration time could be set between 5 to 50 milliseconds with the scanning or sampling time being a corresponding lower amount. In one embodiment, the integration time is 16 milliseconds (ms) and one cluster is sampled every 1 ms. For example, cluster 70 in line 52 is sampled and approximately 1 ms later the pixel cluster 71 in the same line (line 54) is sampled, this process continues until all the clusters in the eight lines are read or sampled. Reading is carried out in a destructive manner, meaning that once the information is readout of a pixel, the pixel is reset.

The signal in a pixel includes two main portions: a background signal and a signal generated as a result of incident x-ray radiation. The background signal is mostly a consequence of 1) "dark current" (a generally unavoidable disturbance that depends on temperature), 2) other parameters, and 3) noise. In some embodiments, a signal conditioning technique called double sampling or correlated double sampling ("DS/CDS") is used to improve the ratio between the signal and background noise. If DS/CDS is used, the pixel's signal is read (the "initial pixel reading"), then the pixel is reset and the reset level is read and subtracted from the initial pixel reading. This methodology helps cancel read-out noise. In some embodiments, DS/CDS is performed on the same chip on which the array of pixels is constructed. The analog values are subtracted and only then converted to a digital signal by an analog-to-digital converter.

The values from each pixel in a pixel cluster are combined. The combined value is evaluated against a predetermined threshold. If the combined value exceeds the threshold, image acquisition is triggered. The way in which values from the pixels are combined, can vary but certain techniques for doing so are described below. Generally, the signal-to-noise ("SNR") ratio of the combined values is relatively low. As a consequence, in one embodiment, combination of the pixel values is carried out in a manner that improves the SNR. The pixel values are integrated. Signals from the pixels are correlated from pixel to pixel and the integration is performed by adding the values. Because the values are correlated from pixel to pixel, when the values are added to each other, noise is averaged out.

The threshold to which the combination or sum of values is compared to is (in one embodiment), a predetermined threshold based on empirical knowledge. For example, the threshold may be a few millivolts or correlated to an x-ray dose of a few μGy (e.g., 5 μGy). In another embodiment, the threshold is determined using an adaptive technique that takes into account temperature, dark current, or both. To ensure that the sensor triggers when it is exposed to x-ray radiation, in one embodiment the sensor 20 is always armed (or turned on). When the sensor is so configured, it will detect x-ray radiation without requiring that the operator activate it.

Figure 3B:
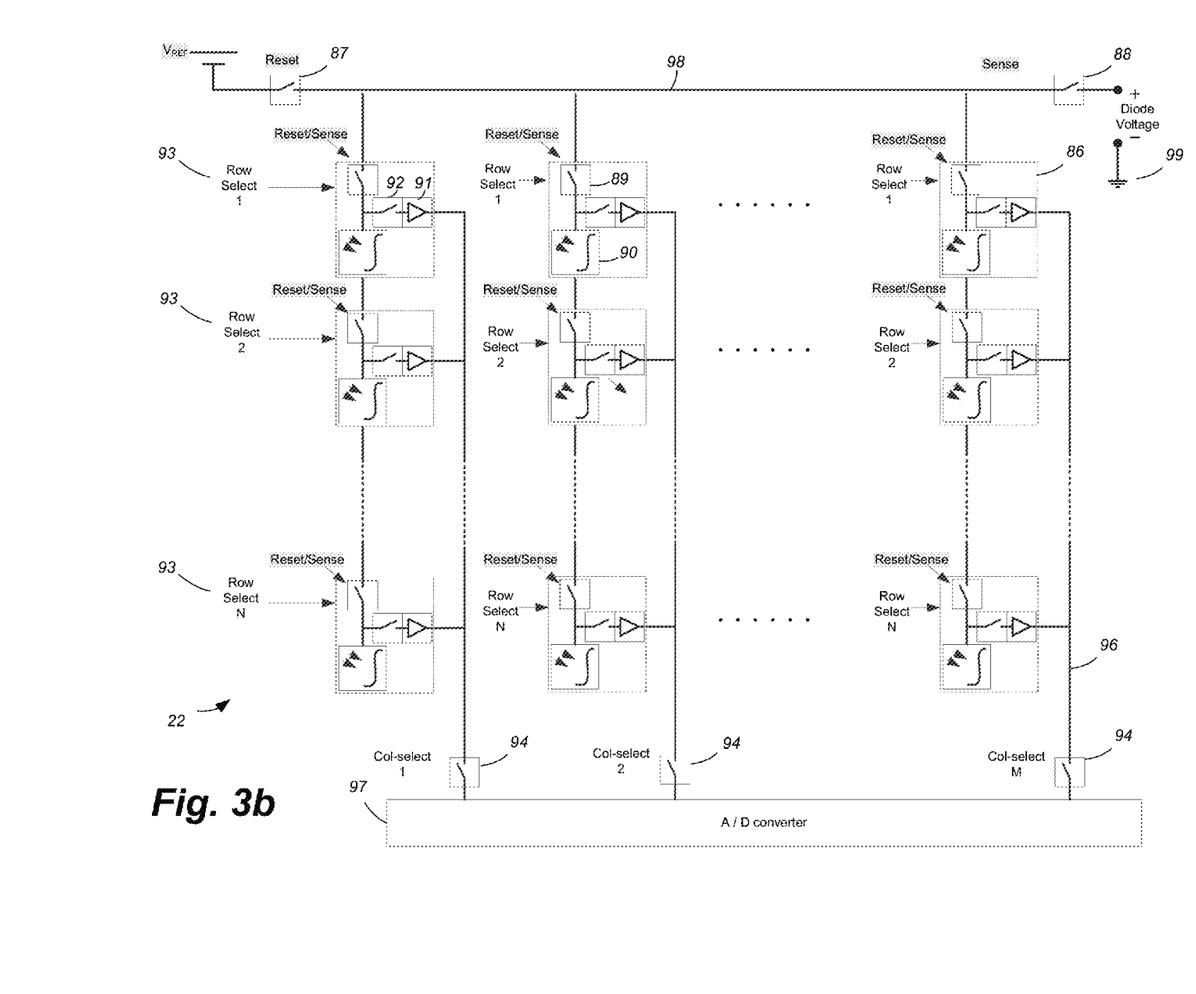
FIG. 3b illustrates a circuit diagram of an array of pixels according to some embodiments of the invention.

FIG. 3b depicts an exemplary diagram of the array of pixels 22. The array of pixels 22 is depicted as an N×M pixel array for explanation purposes; the values of N and M may vary depending on the implementation. The array of pixels 22 includes pixels 86, a reset switch 87, and a sensing switch 88. Each pixel includes a reset/sense switch 89, an integrating element 90, a read-out amplifier 91, and a read-out switch 92. The integrating element 90 integrates charge in response to receiving energy based on x-rays, dark current, and noise, as will be described in more detail below. While we use the term charge in this description, broadly speaking, the charge represents the amount of energy received at the integrating element 90. In other embodiments, electrons, holes, or other electrical signals, whether analog or digital, represent the amount of energy received at the integrating element 90. Each pixel also receives one of the row select lines 93 and column select lines 94. The row select line 93 controls the read-out switch 92. The charge stored on each integrating element 90 is read using the appropriate row select line 93 and column select line 94 and interpreted to generate an x-ray image 40 as described above. The integrating element 90 is erased upon a read out (a "destructive" read). In some embodiments, it is possible for the integrating element 90 to be read out and not erased (a "non-destructive" read), and periodically resetting all or a portion of the array of pixels 22 instead.

The array of pixels 22 has four general function states: 1) a reset state, 2) a detecting state, 3) an integrating state, and 4) a read-out state. In the reset state, the charge stored on the integrating element 90 of each pixel 86 is removed by setting the integrating elements 90 to the reference voltage (e.g., 2 volts). The integrating elements 90 are set to the reference voltage by closing the reset/sense switch 89 and the reset switch 87, while leaving the sensing switch 88 and read-out switch 92 open.

In the detecting state, particular reset/sense switches 89 and the sensing switch 88 are closed to connect particular integrating elements 90 to sensing line 98, while the reset switch 87 and all read-out switches 92 are left open. In the detecting state, the collective charge of the particular pixels selected are measured to determine whether a threshold has been crossed, which may indicate receipt of x-ray radiation. Each integrating element 90 begins with a voltage approximately equal to the reference voltage from the reset state. Thereafter, as charge is integrating at the integrating element 90 from x-ray energy, dark current, and noise, the voltage at the integrating element 90 decreases. Therefore, the collective voltage of the particular pixels selected (referred to as the "diode voltage," since a group of pixels selected can be viewed as a meta diode) measured across the sensing line 98 and ground 99 decreases as the voltage at any integrating element 90 decreases.

To cycle through the pixel clusters 70-85, the sensing switch 88 and the appropriate row select line 93 and column select line 94 are enabled to couple the appropriate pixels 86 to the sensing line 98. For instance, to sense cluster 70: 1) row select line 1 is enabled; and 2) column select lines 1-32 are enabled (cluster 70). To sense cluster 72, row select line 2 is enabled, and the same column select lines remain enabled from sensing cluster 70 (i.e., column select lines 1-32 are enabled). To sense cluster 71, row select line 1 is enabled, and column select lines column select lines M to M-32 are enabled. In some embodiments, additional sensing switches 88 are provided in the array of pixels 22. Each sensing switch 88 is connected to a particular portion of pixels 42 (e.g., one of the pixel rows 52-66) and each sensing switch 88 is associated with its own diode voltage. Thus, multiple pixel clusters 70-85 are sensed simultaneously by sensing the diode voltage of each sense switch, as opposed to cycling through the pixel rows 70-85 one-by-one.

In the integration state, all switches (87, 88, 89, and 92) are open. The array of pixels 22 integrates the charges created by the x-ray radiation as well as by the undesirable noise components (e.g., dark current).

In the read-out state, a signal is provided to a column select line 94 (one from column select lines 1 through M). In addition, a signal is provided along a row select line 93 (one from row select lines 1 through N). In response, the read-out switches of the selected row of pixels is closed. The charge stored on the integrating elements 90 of the row of pixels is output along the output paths 96. The indication provided to the particular column select line 94 serves to chose one of the output paths 96 and allows the charge output along the chosen output path 96 to be input to the A/D converter 97. The A/D converter 97 converts the analog signal received from a pixel and outputs a digital signal to the processor 23. By repeating this process for each pixel 86 through providing signals to the appropriate row select line 93 and column select line 94, the entire array of pixels 22 is read out.

In some embodiments, multiple pixels are read out in parallel. For instance, in some embodiments, the A/D converter 97 converts multiple analog signals from pixels 86 to digital signals simultaneously and forwards the digital signals along a multi-bit bus to the processor 23. In other embodiments, individual pixel A/D converters are provided within each pixel, as opposed to a single A/D converter 97.

Figure 4A:
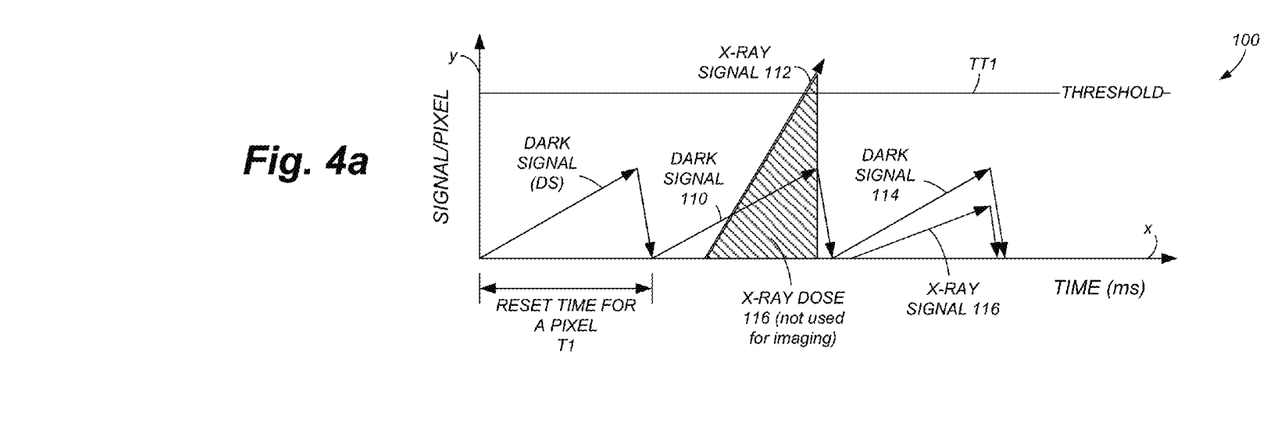
FIGS. 4a and 4b illustrate timing and triggering threshold relationships in an embodiment of the invention where different reset times are used for different sets of pixels to accommodate for the effects of varying x-ray dosages and dark current.
Figure 4B:
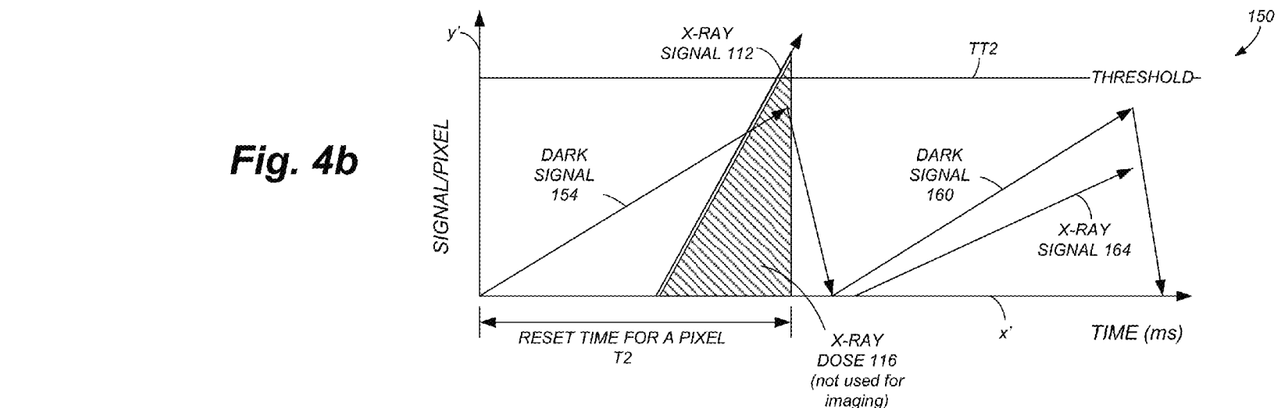

In some embodiments, including the embodiment described in relation to FIGS. 4a-4b, the charge integrating on integrating elements 90 increases (rather than decreases) the voltage stored across each integrating element. In such embodiments, the reset signal removes the stored charge on each integrating element 90 by causing the voltage across each integrating element 90 to be set to ground. Additionally, the diode voltage increases, rather than decreases, as the array of pixels is exposed to x-ray radiation, dark current, and other noise. Thus, the threshold voltage is set to a value above the reset value and is crossed upon the diode voltage increasing to a level above the threshold.

In an alternative embodiment, a variation of the pixel-cluster scanning technique described above is implemented. In the embodiment described above, all of the pixel clusters are read or scanned at the same speed. However, it is possible to read the clusters at different speeds. In one implementation, one group of pixel clusters is read quickly (or fast) (e.g., every millisecond) and the second group of pixel clusters is read slowly (or slow) (e.g., every 10 ms). Both sets of clusters are assigned thresholds (which can be different). In one implementation of this alternative embodiment, the clusters of pixels are located in the same positions as the clusters of perimeter pixels discussed above. However, it is possible that the location of pixel clusters could be different in embodiments that utilize multiple reading speeds.

The concepts used in the multiple-reading-speed alternative are illustrated in FIGS. 4a and 4b. FIG. 4a includes a graph 100. Time is measured on the horizontal axis, X, and signal magnitude is measured on the vertical axis, Y. FIG. 4a illustrates an embodiment with a first, relatively short reset time T1. As is known, dark current is the relatively small electric current that flows through photosensitive devices even when the device is not energized by radiation. Changes in temperature can affect dark current. As shown by the dark signal curve, DS, in FIG. 4a, the magnitude of the pixel or sensor signal due to dark current increases over time. The pixels are periodically reset (e.g., every T1 milliseconds) to remove the dark signal. Otherwise, the dark signal alone could reach a level that meets or exceeds a sensor trigger threshold, TT1. Two circumstances are illustrated in FIG. 4a. In a first circumstance, the sum of a dark signal 110 and an x-ray signal 112 (the signals 110 and 112 are shown overlapping one another, not added to one another) exceeds the threshold TT1. In the second circumstance, the sum of a dark signal 114 and an x-ray signal 116 does not exceed the threshold TT1.

FIG. 4b illustrates a graph 150 with similar axes (X' and Y') as in FIG. 4a., but a relatively long reset time T2. Like FIG. 4a, FIG. 4b illustrates two circumstances. One in which the sum of a dark signal 154 and an x-ray signal 156 exceeds a trigger threshold TT2 and a second in which the sum of a dark signal 160 and an x-ray signal 164 does not exceed the threshold TT2.

As noted above, x-ray doses can vary due to a variety of reasons. Reading certain groups of pixels at different speeds helps compensate for these differences and to adapt to different dose rates. In the FIG. 4a implementation (e.g., the first group of clusters and threshold TT1) a fast read time is used. In other words, the reset time for the pixels is set to a relatively short time. Having a short reset time is particularly useful when the x-ray source is a high dose or high dose rate source, the distance between the x-ray source and the sensor is short, or both. Reducing the reset time helps reduce the possibility of false triggers. However, a short reset time is prudent only when the x-ray signal is relatively strong, as the fast reset time tends to reduce the contribution of the dark signal in the sum of the dark signal and x-ray signal, which as noted above, is the value that is compared to the triggering threshold.

In the FIG. 4b implementation (e.g., the second group of clusters and the threshold TT2) a slow read time is used. In other words, the reset time for the pixels is set to a relatively long time. Having a long reset time is particularly useful when the x-ray source is a low dose source or low dose rate source, the distance between the x-ray source and the sensor is long, or both. Increasing the reset time is prudent when the x-ray signal is relatively low, as the long reset time increases the contribution of the dark signal in the sum of the dark signal and x-ray signal. The increased read time comes at the expense of a lower or slower image detection speed.

Figure 5:
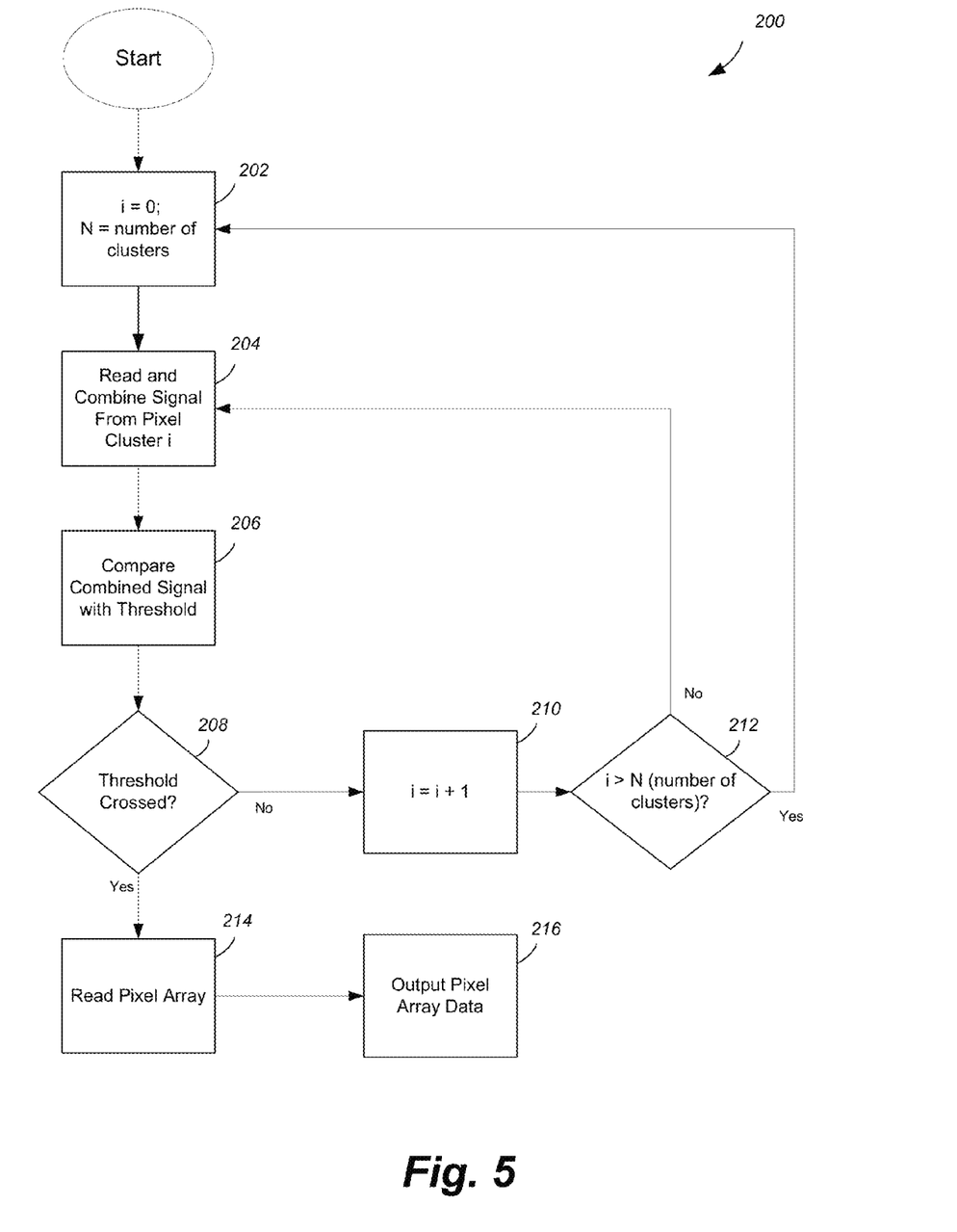
FIG. 5 illustrates a process for automatically triggering an intraoral sensor according to some embodiments of the invention.

FIG. 5 depicts a process 200 for automatically triggering the sensor 20 to capture an image. The process 200 begins in step 202 by resetting parameters such as i and N (i=0; N=number of pixel clusters in the array of pixels 22 to be monitored). In some embodiments, step 202 also includes resetting the array of pixels 22 to remove any dark current, noise, or other undesirable integrated charge using reset switch 87. In step 204, the pixel cluster i (e.g., cluster j) of the array of pixels is read by the processor 23. In FIG. 3, cluster 0 is shown as cluster 70. Proceeding to step 206, processor 23 compares the signal value read from cluster i with a threshold (e.g., threshold TT1 or TT2). In step 208, if the comparison indicates that the threshold has not been crossed, the processor 23 proceeds to step 210 and increments the parameter i. The processor 23 determines in step 212 if the end of the array of pixels has been reached by comparing i with the total number of pixel clusters to be checked in the cycle. If the end of the array of pixels 22 is reached, the processor 23 proceeds back to step 202 and sets i=0 to return to the beginning of the array of pixels 22. If the end of the array of pixels has not yet been reached, the processor 23 returns to step 204 to read the next pixel cluster i. If the processor 23 determines that the threshold has been crossed in step 208, the processor 23 proceeds to read the array of pixels 22 in step 214. Thereafter, the processor 23 outputs the array of pixels data to computer 30.

In some embodiments, to achieve the desired cycle time for cycling through the pixel clusters (e.g., at a rate of 2 ms per pixel cluster), delay counters or similar techniques are incorporated in the process 200. For instance, the processor 23 is operable to delay the pixel reading step 204 until a predetermined time has passed since the previous execution of step 204.

Additionally, as discussed above, different pixel clusters are read at different speeds in some embodiments. In one example, the processor 23 simultaneously executes multiple processes 200, wherein each process 200 implements different delay times, different increment values in step 210, or a combination thereof. Optionally, process 200 is altered to include nested loops to achieve different cycle times for particular pixel clusters. The nested loops use particular delay times, particular increment values in step 210, or a combination thereof to achieve the desired cycle time for pixel clusters.

Thus, the invention provides, among other things, automatic triggering of an x-ray sensor using a selected group of pixels. As should be apparent from the discussion above, there are some limitations associated with certain embodiments of the disclosed triggering techniques. For example, since data from a selected number/position of pixels is used, the trigger threshold is adapted so that the onset of x-rays will be detected even in very low-dose conditions. For instance, in tests involving embodiments of the disclosed sensor, with a lead shield preventing x-rays from reaching two-thirds of the sensor surface, the sensor was successfully triggered both with 480 µGy/s dose rates and with a total dose of 5 µGy. In addition, since the values from a selected number/position of pixels are used, the SNR of the signal created by the sensor is adapted (because the overall sensor signal is low, but the sum of the noise is constant). On the other hand, because the pixels are reset in certain embodiments, the trigger level is stable and does not require adjustments to accommodate for time-dependent effects like accumulating dark signal. Thus, disclosed techniques are relatively impervious to unwanted effects caused by changes in temperature and dark current. Various features and advantages of the invention are set forth in the following claims.

What is claimed is:

1. An intraoral x-ray system comprising:
   an array of pixels, wherein each pixel generates an electrical signal correlated to x-ray radiation that impinges that pixel;
   wherein the array of pixels includes a plurality of pixel clusters including at least a first cluster, a second cluster spaced at a first distance from the first cluster, a third cluster spaced at approximately the first distance from the second cluster, and a fourth cluster spaced at approximately the first distance from the third cluster;
   a processor in communication with the array of pixels; and
   cluster select lines that are selectively enabled to couple the processor to the first cluster, the second cluster, the third cluster, and the fourth cluster to enable the processor to
      read the first cluster, the second cluster, the third cluster, and the fourth cluster, and
      determine an amount of electrical signal generated by each of the first cluster, the second cluster, the third cluster, and the fourth cluster when read,
   wherein the processor reads each pixel of the array of pixels that is exposed to radiation, when the processor determines at least one of the amounts of electrical signal generated crosses a threshold; and
   wherein the processor destructively reads the first cluster, the second cluster, the third cluster, and the fourth cluster one-at-a-time.

2. The x-ray system of claim 1, wherein the first cluster and the second cluster are located proximate to a first side of a perimeter, and the third cluster and the fourth cluster are located proximate to a second side of the perimeter, wherein the second side of the perimeter is opposite of the first side of the perimeter.

3. The x-ray system of claim 1, wherein, when the processor reads an array of pixels, the processor obtains image data from pixels of at least one of the first, second, third, and fourth clusters.

4. The x-ray system of claim 1, wherein
   the second cluster is separated from the first cluster by at least a first pixel,
   the third cluster is separated from the second cluster by at least a second pixel,
   the fourth cluster is separated from the third cluster by a third pixel,
   and none of the first, second, and third pixels is included in the first cluster, the second cluster, the third cluster, or the fourth cluster.

5. The x-ray system of claim 1, wherein each of the pixel clusters is configured to be read non-destructively.

* * * * *